United States Patent
Chauhan et al.

(10) Patent No.: US 7,375,239 B2
(45) Date of Patent: May 20, 2008

(54) METHODS OF SEPARATING ZE-NEPETALACTONE AND EZ-NEPETALACTONE FROM CATNIP OIL

(75) Inventors: Kamlesh R. Chauhan, Laurel, MD (US); Aijun Zhang, Silver Spring, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 538 days.

(21) Appl. No.: 11/007,078

(22) Filed: Dec. 8, 2004

(65) Prior Publication Data

US 2006/0121134 A1    Jun. 8, 2006

(51) Int. Cl.
C07D 311/00 (2006.01)
A61K 36/53 (2006.01)

(52) U.S. Cl. .................................. 549/290; 424/745

(58) Field of Classification Search ............... 424/405, 424/408, 745; 549/290
See application file for complete search history.

(56) References Cited

U.S. PATENT DOCUMENTS

| | | | |
|---|---|---|---|
| 4,663,346 | A | 5/1987 | Coulston et al. |
| 6,524,605 | B1 | 2/2003 | Coats et al. |
| 6,562,332 | B2 | 5/2003 | Baker et al. |
| 6,841,570 | B2 | 1/2005 | Haenke |
| 2003/0138471 | A1 | 7/2003 | Coats et al. |
| 2003/0235601 | A1 | 12/2003 | Hallahan |
| 2004/0127553 | A1 | 7/2004 | Hallahan |

OTHER PUBLICATIONS

McElvain et al , J. Am. Chem. Soc., 1941, vol. 63, p. 1558-1563.*
Smith et al , March's Advanced Organic Chemistry, Reactions, Mechanisms, and Structure, John Wiley & Sons, Inc. 2001, p. 484 and (a total of 3 pages).*
Birkett, Michael A. et al., "Molecules of Interest Aphid Sex Pheromones: From Discovery to Commercial Production," *Photochemistry*, 2003, vol. 62, pp. 651-656.
Chauhan, Kamlesh R. et al., "Iridodials: Enantiospecific Synthesis and Stereochemical Assignment of the Pheromone for the Golden-Eyed Lacewing, *Chrysopa oculata*," *Tetrahedron Letters*, 2004, vol. 45, pp. 3339-3340.
Dawson, Glenn W. et al., "The Aphid Sex Pheromone Cyclopentanoids: Synthesis in the Elucidation of Structure and Biosynthetic Pathways," *Bioorganic & MedicinalChemistry*, 1996, vol. 4, No. 3, pp. 351-361.

(Continued)

Primary Examiner—Taylor Victor Oh
(74) Attorney, Agent, or Firm—John D. Fado; G. Byron Stover

(57) ABSTRACT

A method of separating ZE-nepetalactone and EZ-nepetalactone from catnip oil involving mixing catnip oil dissolved in at least one water immiscible, non-halogenated organic solvent with at least one inorganic base dissolved in water to form a biphasic mixture, stirring the biphasic mixture to hydrolyze ZE-nepetalactone to form ZE-nepetalic acid, separating the aqueous phase containing ZE-nepetalic acid from the organic phase containing EZ-nepetalactone in the biphasic mixture, and optionally acidifying the aqueous phase to about pH 4.5 and adding at least one water immiscible, non-halogenated organic solvent to azeotropically lactonize the ZE-nepetalic acid in the presence of a catalytic amount of p-toluene sulfonic acid to form ZE-nepetalactone.

9 Claims, 4 Drawing Sheets

EZ-nepetalactone

ZE-nepetalactone

OTHER PUBLICATIONS

Hooper, A.M. et al., "Characterization of (1R,4S,4aR, 7S, 7aR)-Dihydronepetalactol as a Semiochemical for Lacewings, Including *Chrysopa* spp. And *Peyerimhoffina gracilis*," *Journal of Chemical Ecology*, Apr. 2002, vol. 28, No. 4, pp. 849-864.

Tucker, Arthur O. et al., "Catnip and the Catnip Response," *Economic Botany*, 1988, vol. 42, No. 2, pp. 214-231.

Zhang, Qing-He et al., "Semiochemistry of the Golden-eyed Lacewing *Chrysopa oculata*: Attraction of Males to a Male-Produced Pheromone," *Journal of Chemical Ecology*, Sep. 2004, vol. 30 No. 9, pp. 1849-1870.

Oliver, James E. et al., "(S)(+)-Linalool from Oil of Coriander," *J. Essent. Oil Research*, Jan./Feb. 2003, vol. 15, pp. 31-33.

Eisenbraun, Edmund J. et al., "(4aS,7S,7aR)-2-(3R,4R,4aR,7S,7aR)-Octahydro-4, 7-dimethyl-1-oxocyclopenta[c]pyran-3yl] nepetalactam: Nitrogen Analogues of Nepetalactone and Nepalic Anhydride," *J. Org. Chem.*, 1988, vol. 53, pp. 3968-3972.

Bottini, Albert T. et al., "(7R)-Trans, Tans-Nepetalactone from Nepeta Elliptica," *Photochemistry*, 1987, vol. 26, No. 4, pp. 1200-1202.

Eisenbraun, Edmund J. et al., "Structure and Stereochemistry of 4aB, 7a,7aB-Nepetalactone from *Nepeta mussini* and its Relationship to the 4aa,7a,7aa-and 4aa,7a,7aB-Nepetalactones from *N. cataria*," J. Org. Chem., 1980, vol. 45, pp. 3811-3814.

Peterson, C.J. et al., "Catnip Essential Oil as a Barrier to Subterranean Termites (Isoptera: Rhinotermitidae) in the Laboratory," *J. Econ. Entomol*, 2003, vol. 96, No. 4, pp. 1275-1282.

Peterson, C.J., et al., "Catnip Essential Oil as a Barrier to Subterranean Termites (Isoptera: Rhinotermitidae) in the Laboratory", J. Economic Entomology, vol. 96(4), pp. 1275-1282, Aug. 2003.

Tucker, A.O., et al., "Catnip and the Catnip Response", Economic Botany, vol. 42(2), pp. 214-231, 1988.

Zhang, Q., et al., "Semiochemistry of the Goldeneyed Lacewing *Chrysopa oculata*: Attraction of Males to a Male-Produced Pheromone", *J. Chemical Ecology*, vol. 30(9), pp. 1831-1853, Sep. 2004.

Oliver, James E., "(S) (+)-Linalool from Oil of Coriander", *J. Essent. Oil Res.*, vol. 15, pp. 31-33, Jan./Feb. 2003.

Birkett, M.A., et al., "Aphid Sex Pheromones: From Discovery to Commercial Production", *Phytochemistry*, vol. 62, pp. 651-656, 2003.

Chauhan, K.R., et al., "Iridodials: Enantiospecific Synthesis and Stereochemical Assignment of the Pheromone for the Golden-Eyed Lacewing, *Chrysopa oculata*", *Tetrahedron Letters*, vol. 45, pp. 3339-3340, 2004.

Dawson, G.W., et al., "The Aphid Sex Pheromone Cyclopentanoids: Synthesis in the Elucidation of Structure and Biosynthetic Pathways", *Bioorganic & Medicinal Chemistry*, vol. 4(3), pp. 351-361, 1996.

Hooper, A.M., et al., "Characterization of (1 R, 4S,4aR,7S,7aR)—Dihydronepetalactol as a Semiochemical for Lacewings, Including *Chrysopa* spp. AND *Peyerimhoffina gracilis*", *J. Chemical Ecology*, vol. 28(4), pp. 849-864, Apr. 2002.

\* cited by examiner

*EZ*-nepetalactone

ZE-nepetalactone

METHODS OF SEPARATING ZE-NEPETALACTONE AND EZ-NEPETALACTONE FROM CATNIP OIL

BACKGROUND OF THE INVENTION

The present invention relates to a method of separating ZE-nepetalactone and EZ-nepetalactone from catnip oil involving mixing catnip oil dissolved in at least one water immiscible, non-halogenated organic solvent with at least one inorganic base dissolved in water to form a biphasic mixture, stirring the biphasic mixture to hydrolyze ZE-nepetalactone to form ZE-nepetalic acid, separating the aqueous phase containing ZE-nepetalic acid from the organic phase containing EZ-nepetalactone in the biphasic mixture, and optionally acidifying the aqueous phase to about pH 4.5 and adding at least one water immiscible, non-halogenated organic solvent to azeotropically lactonize the ZE-nepetalic acid in the presence of a catalytic amount of p-toluene sulfonic acid to form ZE-nepetalactone.

Many natural product components, including terpenes, alkaloids and esters, have potential to either attract or repel insects of broad spectrum. Plant species produce essential oils (aromatic oils) which are used as natural sources of insect repellents and attractants (Hay, R. K. M., Svoboda, K. P., Botany in Volatile Oil Crops: their biology, chemistry and production, Hay, R. K. M., Waterman, P. G. (Eds.), Longman Group UK Limited (1993)). Citronella oil, known for its general repellence towards insects, is obtained from the graminaceous plants *Cymbopogon winterianus* and *C. nardus*. Most of the plants yielding oil of value to the fragrance industry are members of the Labiatae (Lamiaceae) family. Plants of the genus *Nepeta* (catmints) are also members of this family and produce an essential oil which is a minor item of commerce. This catnip oil is very rich in a class of monoterpenoid compounds known as iridoids (Inouye, H., Methods in Plant Biochemistry, 7:99-143 (1991)), more specifically the methylcyclopentanoid nepetalactones and derivatives (Clark, L. J., et al., The Plant Journal, 11:1387-1393 (1997)).

Iridoid monoterpenes have long been known to be effective repellents and/or attractants to a variety of insect species (Eisner, T., Science, 146:1318-1320 (1964); Eisner, T., Science 148: 966-968 (1965); Peterson, C., and J. Coats, Pesticide Outlook, 12:154-158 (2001)). U.S. Pat. No. 4,663,346 disclosed insect repellants with compositions containing bicyclic iridoid lactones (e.g., iridomyrmecin). Further, U.S. Pat. No. 4,869,896 disclosed use of these bicyclic iridoid lactone compositions in potentiated insect repellent mixtures with DEET.

Two nepetalactone isomers exist in catnip oil from catmint, *Nepeta cataria* (Lamiaceae), and can be isolated by distillation (FIG. 1 shows the chemical structures of the naturally-occurring iridoid (methylcyclopentanoid) nepetalactones). One isomer, (4aS, 7S, 7aR)-nepetalactone (cis-trans nepetalactone or ZE-nepetalactone), and its alcohol form (1R, 4aS, 7S, 7aR)-nepetalactol, have been identified as sex pheromones for numerous species of aphids. The isomer (4aS, 7S, 7aS)-nepetalactone (trans-cis nepetalactone or EZ-nepetalactone) is reportedly useful as a cockroach and mosquito repellent (Dawson, G. W., et al., Bioorganic & Medicinal Chemistry, 4(3): 351-361 (1996); Peterson, C. J., and Coats, J., Catnip repels mosquitoes more effectively than DEET, American Chemical Society, 222nd National Meeting (2001); Coats, J., Catnip and Osage orange components found to repel German cockroaches, American Chemical Society, 218th National Meeting (1999)). Since catnip oil has exhibited promising repellent and toxic effects against subterranean termites, nepetalctone isomers are also being evaluated as termiticides (Peterson, C. J., and Elm-Wilson, J., J. Econo. Entomology, 96 (4): 1275-1282 (2003)).

The isomer (4aS, 7S, 7aR)-nepetalactone has been commercially produced in 85-97.5% enantiomeric purity from one selected cultivar of catmint (Birkett, M. A., and J. A. Pickett, Phytochemistry, 62: 651-656 (2003)); this genetically different cultivar of *Nepeta cataria* containing (4aS, 7S, 7aR)-nepetalactone had to be planted and oil obtained from this particular species was used to isolate the ZE-isomer, and therefore is not cost effective. Availability of the other isomer, (4aS, 7S, 7aS)-nepetalactone, still relies on chromatographic separation or chemical synthesis. These traditional methods, chromatographic separation or chemical synthesis of two pure nepetalactone isomers, are labor intensive and expensive. Since both isomers are ecologically important and available from non-specific catnip oil at low price, there is a need for a method that could effectively separate diastereomers of nepetalactones on a large scale and at a low cost.

SUMMARY OF THE INVENTION

In accordance with the present invention there is provided a method of separating ZE-nepetalactone and EZ-nepetalactone from catnip oil involving mixing catnip oil dissolved in at least one water immiscible, non-halogenated organic solvent with at least one inorganic base to form a biphasic mixture, stirring the biphasic mixture to hydrolyze ZE-nepetalactone to form ZE-nepetalic acid, separating the aqueous phase containing ZE-nepetalic acid from the organic phase containing EZ-nepetalactone in the biphasic mixture, and optionally acidifying the aqueous phase to about pH 4.5 and adding at least one water immiscible, non-halogenated organic solvent to azeotropically lactonize the ZE-nepetalic acid in the presence of a catalytic amount of p-toluene sulfonic acid to form ZE-nepetalactone.

DETAILED DESCRIPTION OF THE INVENTION

The present invention relates to a method of separating ZE-nepetalactone and EZ-nepetalactone from catnip oil involving mixing catnip oil dissolved in at least one water immiscible, non-halogenated organic solvent with at least one inorganic base to form a biphasic mixture, stirring the biphasic mixture to hydrolyze ZE-nepetalactone to form ZE-nepetalic acid, separating the aqueous phase containing ZE-nepetalic acid from the organic phase containing EZ-nepetalactone in the biphasic mixture, and optionally acidifying the aqueous phase to about pH 4.5 and adding at least one water immiscible, non-halogenated organic solvent to azeotropically lactonize the ZE-nepetalic acid in the presence of a catalytic amount of p-toluene sulfonic acid to form ZE-nepetalactone.

One embodiment of this invention is an environmentally friendly and economical process of separation of an insect repellent diastereomer, EZ-nepetalactone from commercially available catnip oil.

Another embodiment of this invention is a process of regenerating an important biocontrol agent diastereomer, ZE-nepetalactone, from selectively hydrolyzed ZE-nepetalic acid from the distilled catnip oil.

The invention of this chemical separation process avails both diastereomers of nepetalactones present in nonspecific catnip oil on a large scale and at lower cost.

Figure 1:
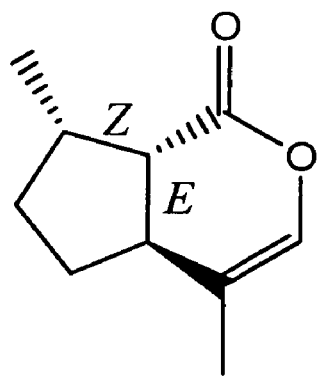
FIG. 1 shows the chemical structures of the naturally-occurring iridoid (methylcyclopentanoid) nepetalactones.
Figure 1:
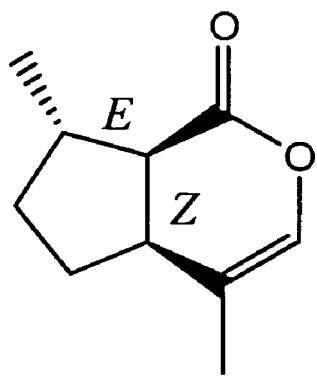
Figure 2:
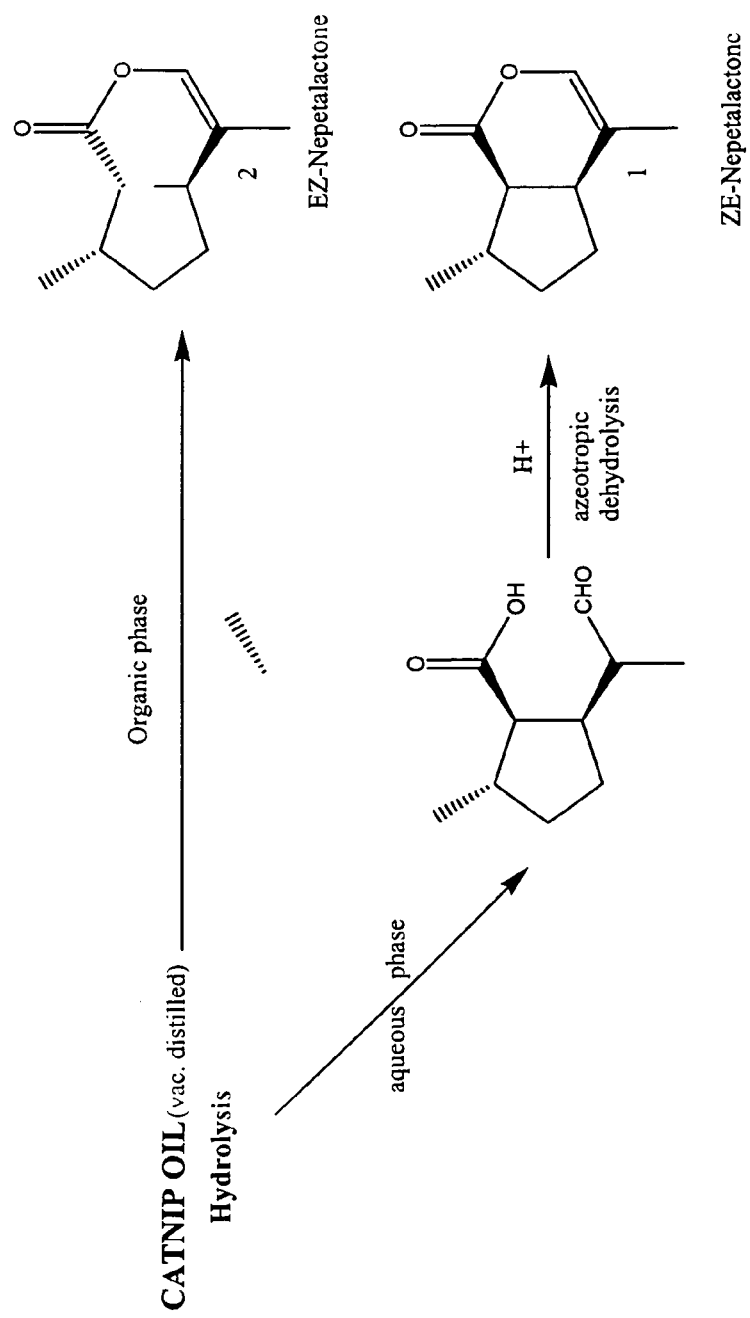
FIG. 2 shows a separation scheme for the nepetalactones.
Figure 3:
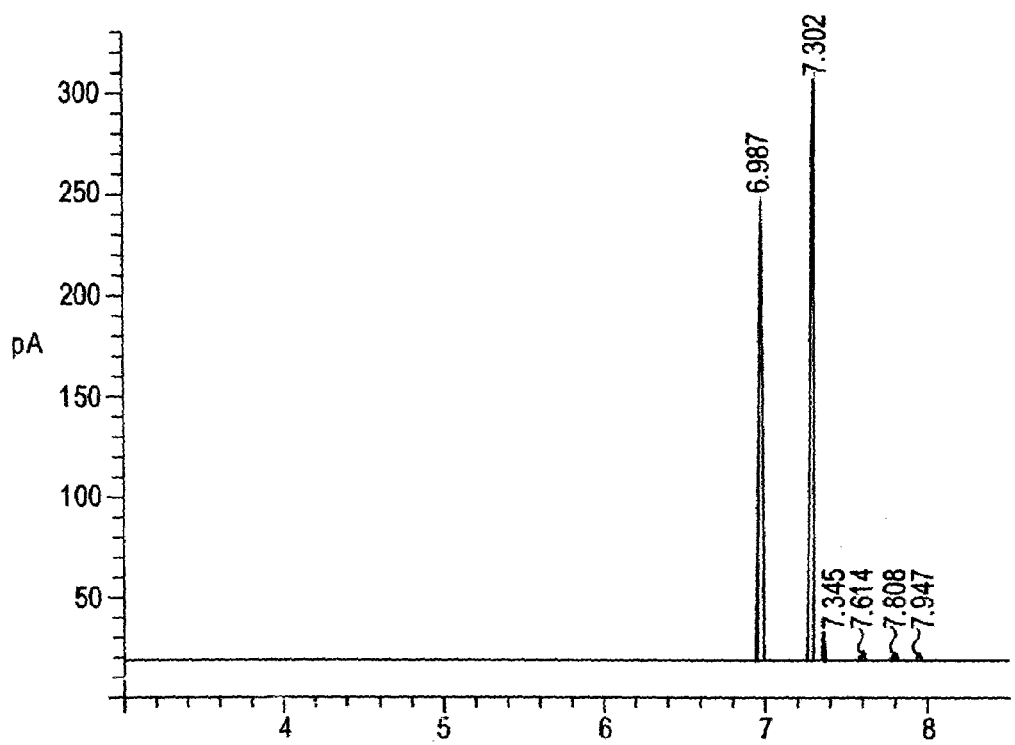
FIG. 3 shows the total ion chromatograms from combined gas chromatography (GC) analysis of a distilled nepetalactone-enriched fraction from commercially-available catmint oil.
Figure 4:
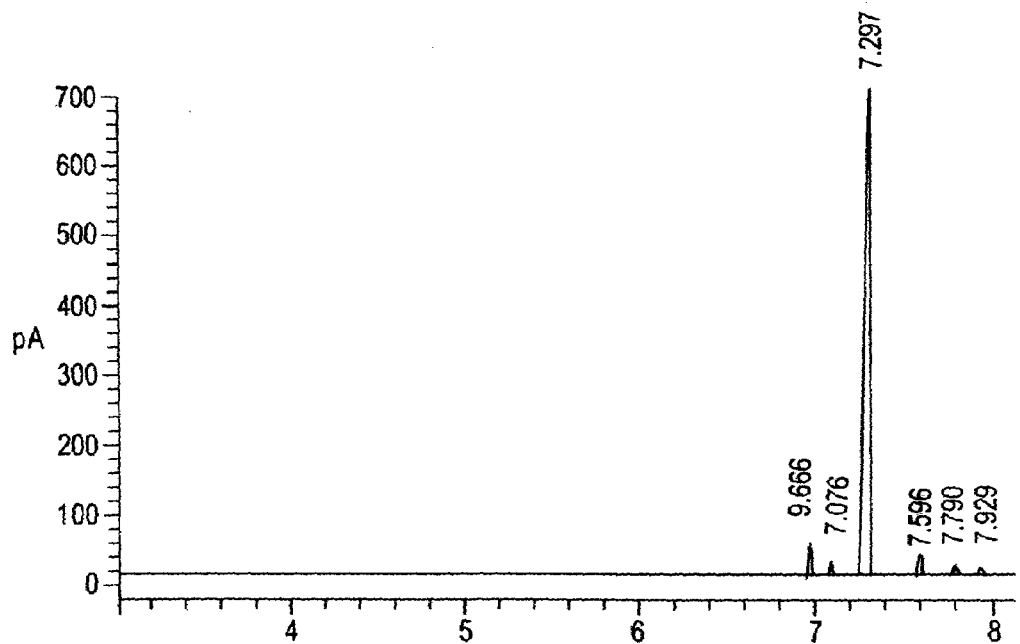
FIG. 4 shows GC analyses of organic phase after 32 hours of biphasic hydrolyses.
Figure 5:
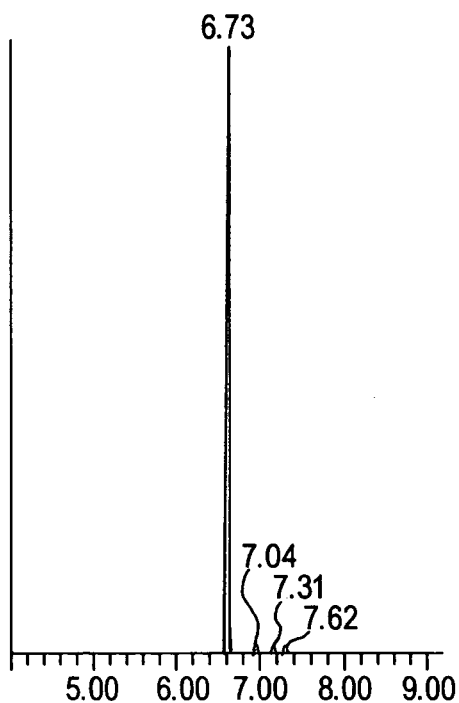
FIG. 5 shows the mass spectra of the major constituents of the E,Z-nepetalactone-enriched organic phase (A) and the Z,E-nepetalactone recovered from aqueous phase (B).
Figure 5:
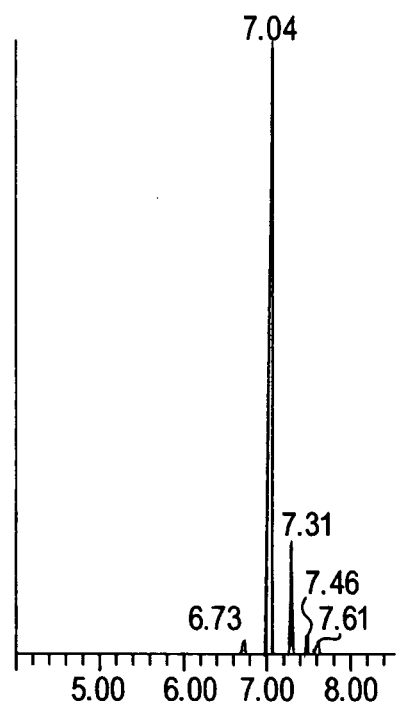
Figure 5:
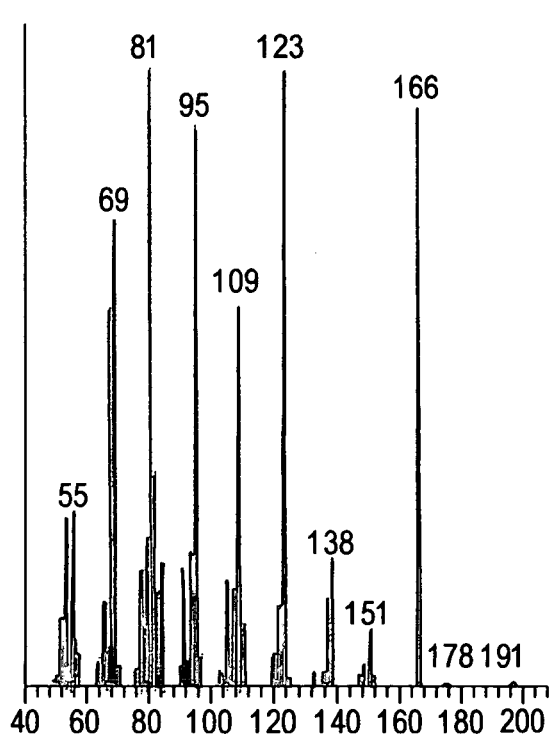
Figure 5:
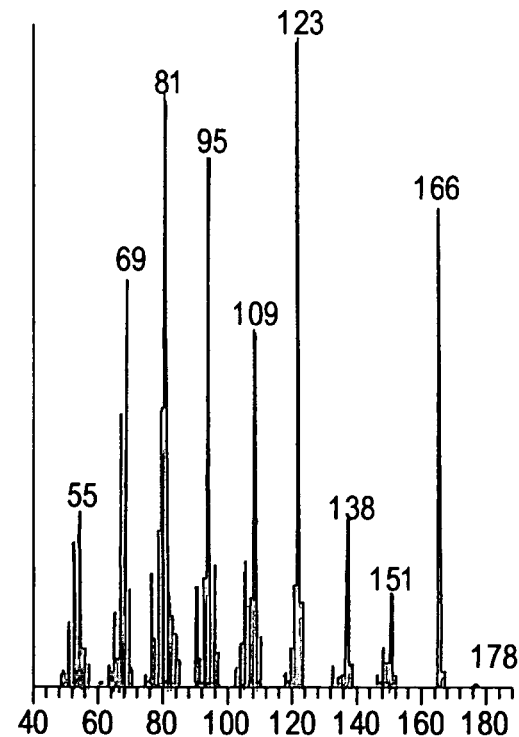

We have surprisingly discovered that under mild basic diphase conditions (4aS, 7S, 7aR)-nepetalactone (ZE) surprisingly selectively hydrolyzed to its corresponding nepetalic acid while the other isomer (4aS, 7S, 7aS)-nepetalactone (EZ) remained in the organic phase which allowed for a separating process which quantitatively separated diastereomers of catnip oil without using harsh chemical conditions or tedious chromatography (see FIG. 2). Subsequently (4aS, 7S, 7aR)-nepetalic acid extracted from the aqueous layer was converted back to the original lactone without changing the stereochemistry. Under optimized experimental conditions, the mixture containing (4aS, 7S, 7aR)- and (4aS, 7S, 7aS)-nepetalactones (distilled from the commercial catnip oil) separated quantitatively at a high purity (>95%). This method can utilize catnip oil from wild catnip plants so that no specific cultivar is required; at the same time, based on the presence of individual isomers of nepetalactone, both isomers can be isolated quantitatively.

Generally, the isomers may be separated by the following method:

Add vacuum distilled catnip containing nepetalactone isomers dissolved in about 2-about 20% w/v (e.g., 2-20% w/v) concentration of a water immiscible, non-halogenated organic solvent (e.g., hexane, ethyl acetate, diethyl ether, petroleum ether, or mixtures thereof) to a three neck flask fitted with a mechanical stirrer, a thermometer and reflux condenser. The commercial catnip oil (e.g., supplied by American Health and Herbs Inc., Philomath, Oreg.) is prepared from *Nepeta cataria* plants and generally contains about 80-88% of nepetalactone isomers, including about 7-13% of B-caryophyllene as major non polar monoterpene; the ratio of ZE and EZ nepetalactone varies in different batches of essential oil, the vacuum distilled catnip oil from American Health and Herbs may contain about 61% of ZE nepetalactone and about 39% of EZ nepetalactone. Vigorously stir the solution and add 0.05-10% w/v concentration of an aqueous solution of an inorganic base (e.g., sodium bicarbonate, lithium hydroxide, potassium hydroxide, sodium carbonate, lithium carbonate, potassium bicarbonate, or mixtures thereof). The temperature of this resulting biphasic mixture is controlled by thermostat at about 45°-about 55° C. (e.g., 40°-55° C.) so that it remains below reflux. For example, during about 32 hours of total stirring the aqueous phase is separated every 8 hours and recharged with equivalent amount of aqueous base. When stirring, only ZE-nepetalactone slowly hydrolyzes to acid, but not the EZ-nepetalactone.

The organic layer is separated from the basic aqueous phase and rinsed with water, then twice rinsed with saturated inorganic base solution (sodium bicarbonate added to distilled water), and finally with saturated sodium chloride (sodium chloride added to distilled water). It is then dried with magnesium sulfate (or sodium sulphate), filtered and concentrated to give clear liquid that is distilled to give EZ-nepetalactone, b.p. 86-90° C./0.5 Torr. Upon cooling the clear oil becomes a white crystalline solid (m.p. 37-39° C.).

Combined aqueous phases are acidified to about pH 4.5 (e.g., by adding 2N HCl solution) and extracted with non-halogenated organic phase (e.g., hexane, ethyl acetate, diethyl ether, petroleum ether, or mixtures thereof). The separated oil is extracted with ethyl acetate (or diethyl ether) in three portions. Combined ethyl acetate fractions are then washed with saturated sodium chloride. It is then dried (with magnesium sulfate, sodium sulphate, or mixtures thereof), filtered and the solvent is stripped on a rotary evaporator to provide thick yellow oil containing ZE-nepetalic acid. The neat ZE-acid is dissolved in toluene (or benzene, or carbon tetrachloride; preferably toluene) and azeotropically lactonized to produce ZE-nepetalactone in the presence of catalytic amount (0.25% of crude ZE-acid) of p-toluene sulfonic acid (Aldrich, Milwaukee, Wis.). Azeotropic dehydration is carried out using Dean and Stark apparatus. Toluene is stripped by distillation, while ZE-nepetalactone is distilled from crude remainder as a clear oil, b.p. 90-92° C./0.5 Torr.

Under these conditions, the mixture containing (4aS, 7S, 7aR)- and (4aS, 7S, 7aS)-nepetalactones (distilled from the commercial catnip oil) are separated quantitatively at a high purity (e.g., >92, preferably >95%, more preferably >98%).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

A three neck flask was fitted with a mechanical stirrer, a thermometer and reflux condenser. 10 grams of vacuum distilled catnip containing nepetalactone isomers dissolved in hexane (2-20% w/v concentration) were added to the flask; the commercial catnip oil was supplied by American Health and Herbs Inc., Philomath, Oreg., and came from *Nepeta cataria* plants and contained 80-88% of nepetalactone isomers, including 7-13% of B-caryophyllene as major non polar monoterpene (the ratio of ZE and EZ nepetalactone varies in different batches of essential oil, the vacuum distilled catnip oil used for this experiment contained 61% of ZE nepetalactone and 39% of EZ nepetalactone). To this vigorously stirred solution was added aqueous solution (0.05-10% w/v concentration) of sodium bicarbonate. The temperature of this resulting biphasic mixture was controlled by thermostat at 50° C. so that it remained below reflux. During 32 hours of total stirring, the aqueous phase was separated every 8 hours and recharged with equivalent amount of aqueous base.

The organic layer was separated from the basic aqueous phase and rinsed with water, then twice rinsed with saturated sodium bicarbonate solution (10 g of sodium bicarbonate was added to 100 ml of distilled water), and finally with saturated sodium chloride (25 g of sodium chloride was added to 100 ml of distilled water). It was then dried with magnesium sulfate, filtered and concentrated to give clear liquid that was distilled to give 4.2 gram of EZ-nepetalactone, b.p. 86-90° C./0.5 Torr. Upon cooling the clear oil became a white crystalline solid (m.p. 37-39° C.)

Combined aqueous phases were extracted with non-halogenated organic phase and acidified to pH 4.5. The separated oil was extracted with ethyl acetate in three portions. Combined ethyl acetate fractions were then washed with saturated sodium chloride. It was then dried with magnesium sulfate, filtered and the solvent was stripped on a rotary evaporator to provide thick yellow oil consisting of ZE-nepetalic acid. The neat ZE-acid was dissolved in toluene and azeotropically lactonized to produce ZE-nepetalactone in the presence of catalytic amount of p-toluene sulfonic acid (Aldrich, Milwaukee, Wis.). Azeotropic dehydration was carried out using Dean and Stark apparatus. Toluene was stripped by distillation, while 5.1 g of ZE-nepetalactone was distilled from crude remainder as a clear oil, b.p. 90-92° C./0.5 Torr.

Under these optimized experimental conditions, 10 grams of the mixture containing (4aS, 7S, 7aR)- and (4aS, 7S, 7aS)-nepetalactones (distilled from the commercial catnip oil) were separated quantitatively at a high purity (>95%).

Analytical Methods: A HP 6890 GC equipped with a 30 m×0.25-mm ID, 0.25-μm film-thickness DB-5 (J&W Scientific Inc., Folsom, Calif.) capillary column in the splitless mode with hydrogen (1.4 ml/min) as carrier was used for analysis. The column temperature program was hold at 100° C. for 2 min, then heated to 250° C. at 15° C./min and held for 5 min. Electron impact mass spectrometry (EI-MS) was conducted on a HP 6890 GC coupled to a HP 5973 Mass Selective Detector using a 60 m×0.25-mm ID, 0.25-μm film-thickness DB-WAXETR capillary column at 100° C. for 2 min, then programmed to 230° C. at 15° C./min and held for 15 min or a 30 m×0.25-mm ID, 0.25-μm film-thickness DB-1 capillary column (50° C. for 2 min, then programmed to 300° C. at 15° C./min and held for 15 min) with helium as carrier gas. A 70 eV electron beam was employed for sample ionization. NMR spectra were recorded in $C_6D_6$ solution on a Bruker QE Plus spectrometer at 300 MHz for $^1H$. The chemical shifts are expressed in ppm relative to the residual solvent for $^1H$ ($C_6H_6$ at δ 7.15 ppm).

This is the first report of selective hydrolyses of two nepetalactone diastereomers under mild basic conditions. Nepetalactones are monoterpene cyclopentanoid compounds and comprises enol-lactone structure fused to cyclopentane ring. The stereochemistry at the junction of cyclopentane and enol-lactone is responsible for the strain and hence the reactivity of nepetalactone isomers. Without being bound by theory, in the case of catnip oil from *Nepeta cataria* the predominant ZE-nepetalactone isomer, the enol-lactone, has lower steric strain and is more susceptible to hydrolyses while the EZ-isomer has higher steric strain and reacts sluggishly towards hydrolyses. In our separation process we took advantage of distinguished molecular properties of these two nepetalactone diastereomers.

In the case of natural abundance of only one nepetalactone isomer in the catnip oil, the separation process can also be conveniently applied for purification. For example, *Nepeta elliptica* species of catmint, a native of India, produces only E,E-nepetalactone along with other monoterpenoids (Bottini, A. L., et al., Phytochemistry, 26(4):1200-1202 (1987)). And based on our discovery this isomer with strained environment of enol-lactone would remain in organic phase when subjected to the present process.

In the case of catnip oil containing only Z,Z-nepetalactone isomer along with other components, only Z,Z-nepetalactone would be hydrolyzed and go into the aqueous phase under the present process. Traditional methods, chromatographic separation or chemical synthesis of two pure nepetalactone isomers, are labor intensive and expensive. Our process, which avoids tedious separation or incidental hazardous waste, is extremely economical: less than $2.5/gram based on our separation from commercial catnip oil versus $160/gram based on HPLC/LC-chromatographic separation at milligram to gram scale and $1000/gram based on chemical syntheses (all three prices were calculated including the cost of raw materials/commercial catnip oil). The present process is efficient at the multigram level and can be easily scaled up for commercial purposes.

The isomer, (4aS, 7S, 7aR)-nepetalactone has previously been commercially produced in 85-97.5% enantiomeric purity from one selected cultivar of catmint (Birkett, M. A., and J. A. Pickett, J. A., Phytochemistry, 62: 651-656 (2003)); however, only one cultivar of *Nepeta cataria* containing (4aS, 7S, 7aR)-nepetalactone could be planted and the oil obtained from this particular species used to isolate the ZE-isomer, therefore the prior art process was not cost effective. Surprisingly, our green separation allows one to use catnip oil from wild catnip plants and thus no specific cultivation is required; at the same time, based on the presence of individual isomers of nepetalactone, one can isolate both isomers quantitatively.

All of the references cited herein are incorporated by reference in their entirety. Also incorporated by reference in their entirety are the following references: Birkett, M. A., and J. A. Pickett, J. A., Phytochemistry, 62: 651-656 (2003); Chauhan, K. R., et al., Tetrahedron Lett. 45: 3339-3340 (2004); Coats, J., Catnip and Osage orange components found to repel Gerrnan cockroaches. Source: American Chemical Society, 218th National Meeting (1999); Dawson, G. W., et al., The aphid sex pheromone cyclopentanoids: Synthesis in the elucidation of structure and biosynthetic pathways, Bioorganic & Medicinal Chemistry, Vol. 4, No. 3, pp 351-361 (1996); Haenke, J. A., et al., Effect of catnip on indigenous Florida subterranean termites, Abstract # 33, 223 rd ACS National Meeting, April 7-11, Orlando, Fla. (2002); Nature's Herbal: Natural Mosquito and Insect Repellent (http://altnature.com/gallery/catnip_mosquito_repellent.htm); Peterson, C. J., Insect Repellents of Natural Origin: catnip and Osage orange, Ph.D. dissertation, Iowa State University, Ames, Iowa (2001); Peterson, C., and J. Coats, J., Catnip repels mosquitoes more effectively than DEET. Source: American Chemical Society, 222nd National Meeting (2001); Tucker, A. O. and S. S. Tucker, S. S., Catnip and the catnip response, Economic Botany, 42(2): 214-231 (1988); Zhang, Q. H., et al., 2004. Semiochemistry of the golden eyed lacewing *Chrysopa oculata* (Neroptera:Chrysopidae): Attraction of males to male produced pheromone, J. Chem. Ecol., 30: 1831-1852 (2004). Also incorporated by reference in their entirety are the following U.S. Pat. Nos. 6,562,332; 6,524,605; 4,663,346. Also incorporated by reference in their entirety are the following published U.S. Patent Applications: 20040127553; 20040024054; 20030225290; 20030138471; 20030235601.

Thus, in view of the above, the present invention concerns (in part) the following:

A method of separating ZE-nepetalactone and EZ-nepetalactone from catnip oil, comprising (or consisting essentially of or consisting of) mixing catnip oil dissolved in at least one water immiscible, non-halogenated organic solvent with at least one inorganic base (dissolved in water) to form a biphasic mixture, stirring said biphasic mixture to hydrolyze ZE-nepetalactone to form ZE-nepetalic acid, separating the aqueous phase containing ZE-nepetalic acid from the organic phase containing EZ-nepetalactone in said biphasic mixture, and optionally acidifying the aqueous phase to about pH 4.5 and adding at least one water immiscible, non-halogenated organic solvent to azeotropically lactonize said ZE-nepetalic acid in the presence (of a catalytic amount) of p-toluene sulfonic acid to form ZE-nepetalactone.

The above method, wherein said water immiscible, non-halogenated organic solvent is selected from the group consisting of hexane, ethyl acetate, diethyl ether, petroleum ether, and mixtures thereof.

The above method, wherein said water immiscible, non-halogenated organic solvent is hexane.

The above method, wherein said inorganic base is selected from the group consisting of lithium hydroxide, potassium hydroxide, sodium carbonate, lithium carbonate, potassium bicarbonate, sodium bicarbonate, and mixtures thereof.

The above method, wherein said inorganic base is sodium bicarbonate.

The above method, wherein said biphasic mixture is stirred at a temperature of about 45°-about 55° C.

The above method, comprising (or consisting essentially of or consisting of) acidifying said aqueous phase to about pH 4.5 and adding at least one water immiscible, non-halogenated organic solvent to azeotropically lactonize said ZE-nepetalic acid in the presence of p-toluene sulfonic acid to form ZE-nepetalactone.

The above method, comprising (or consisting essentially of or consisting of) acidifying said aqueous phase to about pH 4.5 by adding 2N HCl solution to said aqueous phase and adding at least one water immiscible, non-halogenated organic solvent to azeotropically lactonize said ZE-nepetalic acid in the presence of p-toluene sulfonic acid to form ZE-nepetalactone.

The above method, comprising (or consisting essentially of or consisting of) mixing catnip oil dissolved in about 2-about 20% w/v concentration of at least one water immiscible, non-halogenated organic solvent with about 0.05-about 10% w/v concentration of at least one inorganic base to form a biphasic mixture, stirring said biphasic mixture to hydrolyze ZE-nepetalactone to form ZE-nepetalic acid, separating the aqueous phase containing ZE-nepetalic acid from the organic phase containing EZ-nepetalactone in said biphasic mixture, and optionally acidifying the aqueous phase to about pH 4.5 and adding at least one water immiscible, non-halogenated organic solvent to azeotropically lactonize said ZE-nepetalic acid in the presence of p-toluene sulfonic acid to form ZE-nepetalactone.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method of separating ZE-nepetalactone and EZ-nepetalactone from catnip oil, comprising mixing catnip oil dissolved in at least one water immiscible, non-halogenated organic solvent with at least one inorganic base to form a biphasic mixture, stirring said biphasic mixture to hydrolyze ZE-nepetalactone to form ZE-nepetalic acid, separating the aqueous phase containing ZE-nepetalic acid from the organic phase containing EZ-nepetalactone in said biphasic mixture, and optionally acidifying the aqueous phase to about pH 4.5 and adding at least one water immiscible, non-halogenated organic solvent to azeotropically lactonize said ZE-nepetalic acid in the presence of p-toluene sulfonic acid to form ZE-nepetalactone.

2. The method according to claim 1, wherein said water immiscible, non-halogenated organic solvent is selected from the group consisting of hexane, ethyl acetate, diethyl ether, petroleum ether, and mixtures thereof.

3. The method according to claim 1, wherein said water immiscible, non-halogenated organic solvent is hexane.

4. The method according to claim 1, wherein said inorganic base is selected from the group consisting of lithium hydroxide, potassium hydroxide, sodium carbonate, lithium carbonate, potassium bicarbonate, sodium bicarbonate, and mixtures thereof.

5. The method according to claim 1, wherein said inorganic base is sodium bicarbonate.

6. The method according to claim 1, wherein said biphasic mixture is stirred at a temperature of about 45°-about 55° C.

7. The method according to claim 1, comprising acidifying said aqueous phase to about pH 4.5 and adding at least one water immiscible, non-halogenated organic solvent to azeotropically lactonize said ZE-nepetalic acid in the presence of p-toluene sulfonic acid to form ZE-nepetalactone.

8. The method according to claim 1, comprising acidifying said aqueous phase to about pH 4.5 by adding 2N HCl solution to said aqueous phase and adding at least one water immiscible, non-halogenated organic solvent to azeotropically lactonize said ZE-nepetalic acid in the presence of p-toluene sulfonic acid to form ZE-nepetalactone.

9. The method according to claim 1, comprising mixing catnip oil dissolved in about 2-about 20% w/v concentration of at least one water immiscible, non-halogenated organic solvent with about 0.05-about 10% w/v concentration of at least one inorganic base to form a biphasic mixture, stirring said biphasic mixture to hydrolyze ZE-nepetalactone to form ZE-nepetalic acid, separating the aqueous phase containing ZE-nepetalic acid from the organic phase containing EZ-nepetalactone in said biphasic mixture, and optionally acidifying the aqueous phase to about pH 4.5 and adding at least one water immiscible, non-halogenated organic solvent to azeotropically lactonize said ZE-nepetalic acid in the presence of p-toluene sulfonic acid to form ZE-nepetalactone.

* * * * *